(12) United States Patent
Hopenfeld

(10) Patent No.: US 12,408,875 B2
(45) Date of Patent: Sep. 9, 2025

(54) ADAPTIVE CORRELATION METHODS FOR HEARTBEAT DETECTION

(71) Applicant: Bruce Hopenfeld, New Harmony, UT (US)

(72) Inventor: Bruce Hopenfeld, New Harmony, UT (US)

(*) Notice: Subject to any disclaimer, the term of this patent is extended or adjusted under 35 U.S.C. 154(b) by 224 days.

(21) Appl. No.: 18/092,882

(22) Filed: Jan. 3, 2023

(65) Prior Publication Data

US 2023/0210467 A1 Jul. 6, 2023

Related U.S. Application Data

(60) Provisional application No. 63/416,628, filed on Oct. 17, 2022, provisional application No. 63/401,765, filed on Aug. 29, 2022, provisional application No. 63/320,809, filed on Mar. 17, 2022, provisional application No. 63/296,206, filed on Jan. 4, 2022.

(51) Int. Cl.
*A61B 5/00* (2006.01)
*A61B 5/352* (2021.01)

(52) U.S. Cl.
CPC .............. *A61B 5/721* (2013.01); *A61B 5/352* (2021.01); *A61B 2562/0219* (2013.01)

(58) Field of Classification Search
CPC . A61B 5/721; A61B 5/352; A61B 2562/0219; A61B 5/349; A61B 5/361; A61B 5/364
See application file for complete search history.

(56) References Cited

U.S. PATENT DOCUMENTS 9,402,557 B2 * 8/2016 Hopenfeld ............. A61B 5/352

FOREIGN PATENT DOCUMENTS

WO WO-2022086740 A1 * 4/2022 ........... A61B 5/0245

* cited by examiner

*Primary Examiner* — Scott M. Getzow
(74) *Attorney, Agent, or Firm* — Bruce Hopenfeld

(57) ABSTRACT

A method for detecting heart beats is disclosed. A plurality of sensors are configured to receive a cardiac signal and another cardiac signal or a signal correlated with a noise source. A processor is configured to detect candidate peaks in a cardiac signal and select a subset of the candidate peaks for temporal correlation with features, such as peaks, in another cardiac signal or noise correlated signal. This relationship is quantified by a correlation measure. The correlation measure, in turn, influences the likelihood that a particular peak or sequence corresponds to a heartbeat. Candidate peaks that were not part of the correlation process may then be added to a sequence or sequences associated with the peaks subject to the correlation analysis. Sequences are scored according to quality and a final sequence is selected as possible heartbeats.

44 Claims, 10 Drawing Sheets

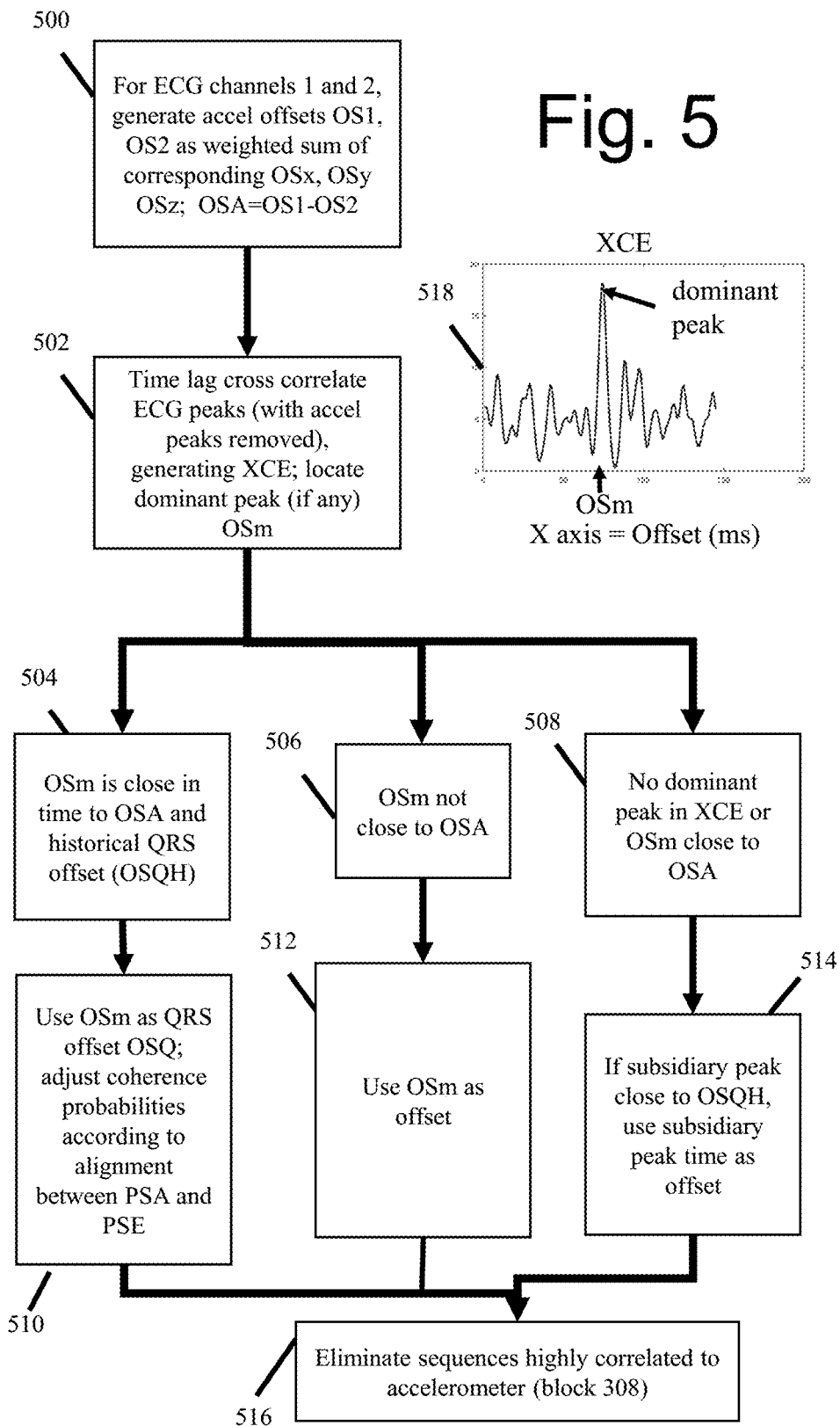

ADAPTIVE CORRELATION METHODS FOR HEARTBEAT DETECTION

PRIORITY CLAIM

This application claims priority to: U.S. Provisional Patent Application Ser. No. 63/296,206, filed on Jan. 4, 2022, 2022, U.S. Provisional Patent Application Ser. No. 63/320,809, filed on Mar. 17, 2022, U.S. Provisional Patent Application Ser. No. 63/401,765, filed on Aug. 29, 2022, and U.S. Provisional Patent Application Ser. No. 63/416,628, filed on Oct. 17, 2022.

TECHNICAL FIELD

The invention pertains primarily to cardiac monitoring, and in particular heartbeat detection in single or multi-channel cardiac signals such as electrocardiograms.

BACKGROUND ART

The continued evolution of wearable sensors and portable electronics will likely result in the substantial growth of long term day-to-day cardiac monitoring. Important aspects of cardiac monitoring include the estimation of heart rate and the detection of atrial fibrillation. Despite the advances in wearable sensors, noise remains a significant problem. In situations where an exogeneous, noise correlated (e.g. accelerometer) signal is available, there are a variety of prior art techniques for processing the exogeneous signal in an attempt to remove the noise. Such methods include adaptive cancellation and wavelet coefficient removal.

V. Nathan and R. Jafari describe a scheme for weighting the probability of a heart rate according to an accelerometer power spectrum, "Particle Filtering and Sensor Fusion for Robust Heart Rate Monitoring Using Wearable Sensors," in *IEEE Journal of Biomedical and Health Informatics*, vol. 22, no. 6, pp. 1834-1846, November 2018, doi: 10.1109/JBHI.2017.2783758. Lanata et al. "A Novel Algorithm for Movement Artifact Removal in ECG Signals Acquired from Wearable Systems Applied to Horses", *PLoS ONE* 10(10): e0140783, analyze accelerometer signals to determine when motion artifacts may occur in an ECG signal, and analyze statistics on these sections to identify portions of the signal whose shape deviates from the normal heartbeat ECG shape. These noise related components of these portions are removed with an adaptive filter.

The present inventor's previous work includes sequence generation and scoring of multi-channel signals, which is described in publication WO/2022/086740, entitled "Multichannel Heartbeat Detection by Temporal Pattern Search." Also, U.S. Pat. No. 9,402,557, issued Aug. 2, 2016 to the present inventor, describes systems and methods for detecting sequences of heartbeats in noisy signals by performing combinatorial optimization on peak temporal regularity within a single channel. The '557 patent describes a method than can handle high noise in a single channel by performing a combinatorial sequence search on a relatively large number of candidate peaks that may correspond to mutually exclusive sequences.

Heartbeat likelihood measures based on peak prominence are prior art due to the work of the present inventor and, for example, "An innovative method based on Shannon energy envelope and summit navigation for detecting R peaks of noise stress test signals," *J Electrocardiol*. 2021 March-April; 65:8-17, by Van Manh H, Nguyen N V, Thang P M.

The prior art also describes cross correlation of an ECG signal with a shape template (e.g. of the QRS complex) for the purpose of determining the shape match between ECG features and the template. (See e.g. Last et al., "Multicomponent based cross correlation beat detection in electrocardiogram analysis", *BioMed Eng OnLine* 3, 2004). Simultaneous cross-correlation of ECG leads for the purpose of determining beat quality has been described by Morgado et al. in "Quality estimation of the electrocardiogram using cross-correlation among leads," *Biomed Eng Online*, 2015.

The prior art includes a variety of methods for temporally correlating multi-modal cardiac data by correcting for delays (offsets) between different data streams. An overview of many methods is described by Silva et al. in "Robust detection of heart beats in multimodal data," *Physiol Meas.* 2015 August; 36(8):1629-44. A common technique for compensating for different peak/feature times in different types of signals, e.g. between an ECG R peak and a peak in an arterial blood pressure signal, involves addition of a fixed delay to one set of peak times. A more involved method from Pangerc and Jager involves estimating the relationship between pulse rate and the pulse transit time with a univariate regression. The offset with the highest correlation measure is chosen, and used to match peaks in the two different types of signals. ("Robust detection of heart beats in multimodal records using slope- and peak-sensitive band-pass filters." *Physiological Measurement* 36.8 (2015): 1645.) However, Pangerc and Jager separate clean ECG sections from noisy ones; it is not clear how this technique would work in the context of signals that are mostly or entirely noisy.

More generally the prior art lacks robust measures for determining the temporal relationship between features of one signal and features of another signal in the case of high noise when the temporal relationship of those features is not known a priori. With regard to cancellation of motion artifacts in an ECG signal that may be associated with an accelerometer signal, cancellation at the frequency level may result in throwing out valuable information in the ECG. Reliance on shape criteria to remove motion artifacts as described e.g. by Lanata et al. will not work when the motion artifact shapes cannot be distinguished from QRS complexes.

With regard to multi-channel heartbeat signals, the prior art does not disclose detailed methods for finding heartbeat peak time offsets between noisy channels that are not known a priori. On the fly determination of these peak time offsets permits a robust and flexible implementation of the multi-channel heartbeat detection methods described in WO/2022/086740, entitled "Multichannel Heartbeat Detection by Temporal Pattern Search."

DISCLOSURE OF INVENTION

The present invention overcomes the limitations of the prior art by searching for time lagged temporal patterns between a noisy cardiac signal and another cardiac signal or a noise correlated signal such as an accelerometer. Temporal patterns are analyzed by detecting candidate peaks in a cardiac signal and selecting a subset of the candidate peaks for temporal correlation with features, such as peaks, in another cardiac signal or noise correlated signal. This relationship is quantified by a correlation measure. The correlation measure, in turn, influences the likelihood that a particular peak or sequence corresponds to a heartbeat. Candidate peaks that were not part of the correlation process may then be added to a sequence or sequences associated with the peaks subject to the correlation analysis.

If the two signals are cardiac signals and there is a relatively high temporal similarity measure between corresponding peaks in the first two signals, the peaks may be considered to have a relatively higher likelihood of being cardiac peaks unless the similarity can be attributed to a common noise source. Conversely, if one signal is a cardiac signal and the other an accelerometer signal, a relatively high temporal similarity measure between corresponding peaks in the first two signals suggests a low likelihood that the peaks in the cardiac signal are heartbeats (because they are correlated to a noise source).

Specifically, a plurality of sensors are configured to receive a cardiac signal and another signal, which may be either a cardiac signal or a signal correlated to a noise source. A processor is configured to preprocess the cardiac signal and then detect candidate peaks that may correspond to mutually exclusive heartbeat sequences. A subset of these candidate peaks, which either corresponds to part of a possible heartbeat sequence or correspond to the N best individual peaks, is then chosen for temporal correlation.

Specifically, these selected peaks in one signal are temporally correlated with the selected peaks in another signal. If there is a high degree of correlation between the peaks and one of the signals is an accelerometer signal, correlation suggests that the correlated peaks in the cardiac signal are noise. In this case, the noise peaks are removed, and heartbeat selection proceeds accordingly. In particular, peak sequences are generated from remaining peaks and scored according to temporal regularity, peak prominence, and skips. The peak prominence measure is determined as if the removed peaks did not exist.

If both of the signals are cardiac signals and there is a high degree of correlation between the peaks, the correlated peaks are more likely to be true heart beats. Peak sequences are generated from these peaks, and the sequence scores reflect the higher likelihood that the correlated peaks are heart beats. These peak sequences may include candidate peaks that were not part of the correlation analysis.

Final heartbeat/sequence selection is based on the scores associated with final sequences.

BRIEF DESCRIPTION OF DRAWINGS

FIG. 5 is a flowchart of the preferred method for obtaining multi-channel ECG peak coherence times in the context of accelerometer peak cancellation.

BEST MODE FOR CARRYING OUT THE INVENTION

Matlab and set notation are generally used herein.

As used herein, a "peak" is a fiducial point within a portion of a cardiac signal. A raw cardiac signal may be processed through any number of differencing filters which correspond to potentially different maxima, minima or zero-crossings. Any of these different maxima, minima or zero-crossings, or functions (e.g. linear combinations) thereof, can be a "peak."

"RR interval" refers to the time between sequence elements.

The detection of a "cardiac rhythm" refers to obtaining information regarding a heart's RR intervals. Such information includes, without limitation, detection of sequences of heartbeats, estimation of average RR interval over a period, and obtaining histograms regarding the likelihood of RR interval distributions.

"Signal" means an analog or digital representation of a physical process. The result of processing a signal, whether by filtering, differencing or otherwise, is a signal, providing that the processing preserves at least some information. The representation of a physical process may be in a highly abstract form. For example, as described below, a synthetic signal is created by creating shapes (e.g. triangles) centered on peak times.

"Temporal correlation" means that the timing relationship of a portion of one signal with a portion of another signal confers information regarding whether the signal portions correspond to either the same physical event (e.g. a particular heartbeat) or related physical events (e.g. motion that causes a particular artifact to be recorded at a sensor).

"Mutually exclusive" sequences means that, for first and second sequences, if all the peaks in the first sequence are considered as true heartbeats, at least half of the beats in the second sequence are physiologically unlikely to be true heartbeats.

The present invention will generally be described with reference to electrocardiographic signals. However, the principles herein are directly applicable to a variety of cardiac signals. For example, the envelope extracted from a related set of ultrasound images is a cardiac signal if it contains information regarding the heartbeat cycle.

Figure 1:
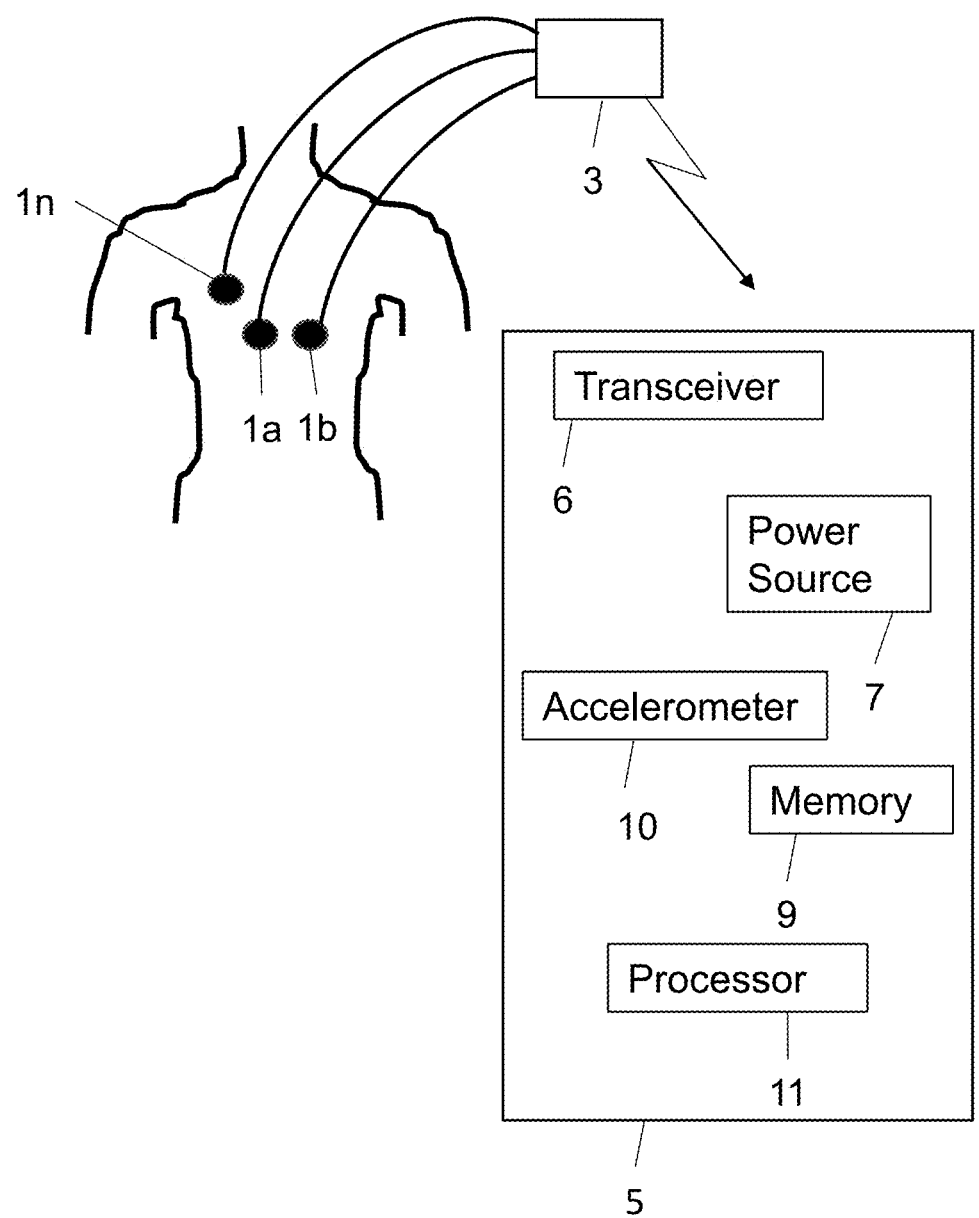
FIG. 1 shows one possible context within which the present invention may be carried out.

FIG. 1 shows one possible context within which the present invention may be carried out. A plurality of sensors, electrodes 1a, 1b . . . 1n, are disposed on the torso of a human body. The present invention is not limited to humans. The electrodes 1a-1n are connected to a recorder 3, which records the voltage signals therebetween. The recorder 3 may implement the cardiac analysis features of the present invention, or it may wirelessly transmit the recorded signals, after varying degrees of amplification, filtering and other processing, to a monitor 5. The monitor 5 comprises a transceiver 6 that receives signals from the recorder 3. The signals are stored in a memory 9, and processed according to the methods described herein by the processor 11. A power source 7 provides energy to the monitor 5. The monitor 5 also comprises a 3 axis accelerometer 10. More details on various hardware components associated with recorder 3 and processor 5 may be found in Chen et al., "Body Area Networks: A Survey," Mobile Networks and Applications, April 2011, Volume 16, Issue 2, pp 171-193, which is incorporated by reference herein. In no way is the present invention limited to body area networks.

Figure 2:
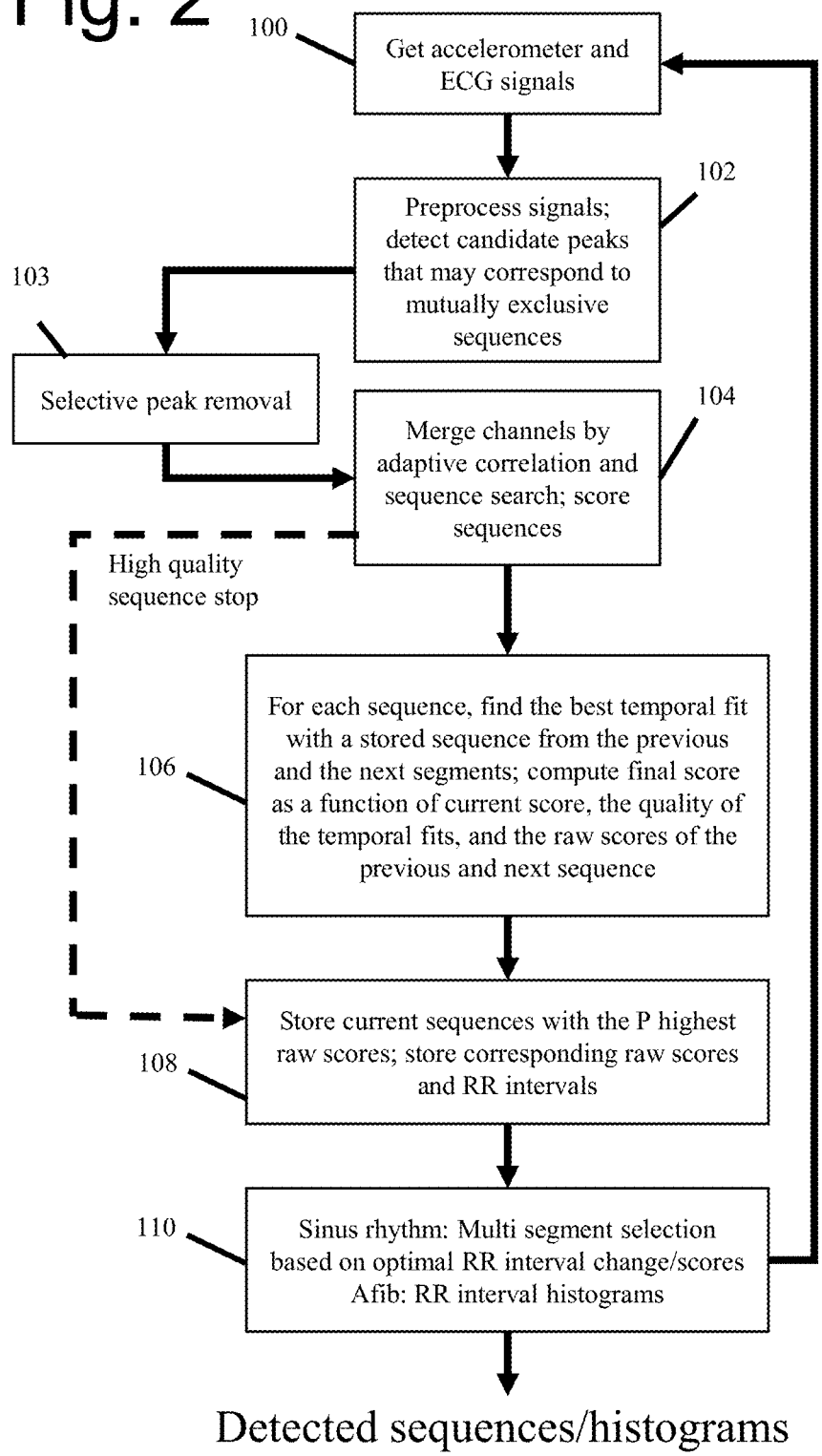
FIG. 2 is a high level flow chart of a multi-channel cardiac rhythm detection method based upon removal of ECG peaks that are correlated with accelerometer peaks and adaptive correlation of multiple cardiac signals.

FIG. 2 is a high level flow chart of a multi-channel cardiac rhythm detection method based upon removal of ECG peaks that are correlated with accelerometer peaks and adaptive correlation of multiple cardiac signals. Each segment is preferably 5 seconds long, although segment length may increase or decrease for low or high heart rates respectively. In block 100, digital signals are acquired from ECG channels corresponding to the electrodes 1a . . . 1n in FIG. 1. A digital signal is also acquired from the accelerometer 10. In block 102, the signals are preprocessed by low pass filtering with a cutoff of 45 Hz and resampling to a rate of 256 samples/second. Candidate peaks are selected according to peak quality criteria. For a five second segment, a preferred range for the number of candidate peaks is 20-30. In high noise conditions, the candidate peaks may correspond to mutually exclusive sequences.

Additional preprocessing includes generating a discrete cosine transform of the signals and examining the power spectrum. If there is substantial power above approximately 10 Hz indicative of disorganization, the segment in question is not further processed.

Control transfers to block 103, which implements the methods described with reference to FIG. 10 and otherwise herein to selectively remove ECG peaks in a variety of circumstances. In particular, peak removal applies to: 1) peaks correlated with accelerometer peaks; 2) in the case of fetal ECG processing, peaks correlated to maternal QRS complexes; 3) peaks that exceed an estimate of the acceptable dynamic range of the QRS complex; and 4) other circumstances. In the preferred embodiment, selective removal means that peaks can't form part of parent heartbeat sequences (defined below) and that those peaks do not count as noise peaks in the peak prominence SNR measure described in publication WO/2022/086740, entitled "Multi-channel Heartbeat Detection by Temporal Pattern Search," which is herein incorporated by reference. In some circumstances, as described below, removed accelerometer related peaks may be added to parent sequences. In an alternative embodiment, instead of selective removal of peaks, peaks may be assigned a non-binary heartbeat likelihood measure, and potentially form part of heartbeat sequences and/or at least partially contribute to the peak prominence SNR measure. Further, although the preferred embodiment involves processing sets of peaks, some of the peak removal/QRS likelihood assignment methods described herein may be applied to serial peak processing. In the case of high precision, real time detection (e.g. in the MRI context), the present invention may be implemented so as to predict the timing of a next QRS complex based on analysis of prior signal portions.

As described in the abovementioned multi-channel patent publication, in block 104, separately for each channel, possible heartbeat peaks are detected and disjoint/overlapping sequences formed therefrom unless and until a high quality sequence is found, in which case control passes to block 108, as indicated by the dashed line. According to the present invention, separate channels are merged according to adaptive correlation, as will be described below. Single channel sequence quality is assessed according to previously described criteria. Absent finding a high quality sequence, possible peaks across all channels are grouped together and candidate heartbeat sequences formed therefrom. A raw score is assigned to all sequences, the single channel and combined channel sequences.

In block 106, for the stored sequences from the prior segment, the best temporal fit is found with a stored sequence from its prior segment and the current segment. For 5 second segments, the temporal fit is the temporal regularity score of a merged 5 second segment formed from the second and first 2.5 second subsegments respectively of consecutive segments. The final score of a sequence is equal to its raw score plus the raw scores of the previous and next sequences weighted by the qualities of the temporal fits.

In block 108, the current segment's P sequences with the highest raw scores are stored. The raw scores are also stored. In block 110, for sinus rhythm, an optimal path (selected sequences) through the segments may be determined by maximizing (e.g. by combinatorial optimization or the Viterbi algorithm) the path probability based on sequence scores and segment to segment changes in RR interval. Smaller changes in RR intervals are associated with higher probabilities. With regard to atrial fibrillation, instead of selecting particular sequences, the system may maintain a histogram of RR intervals weighted by heartbeat likelihood.

Figure 3:
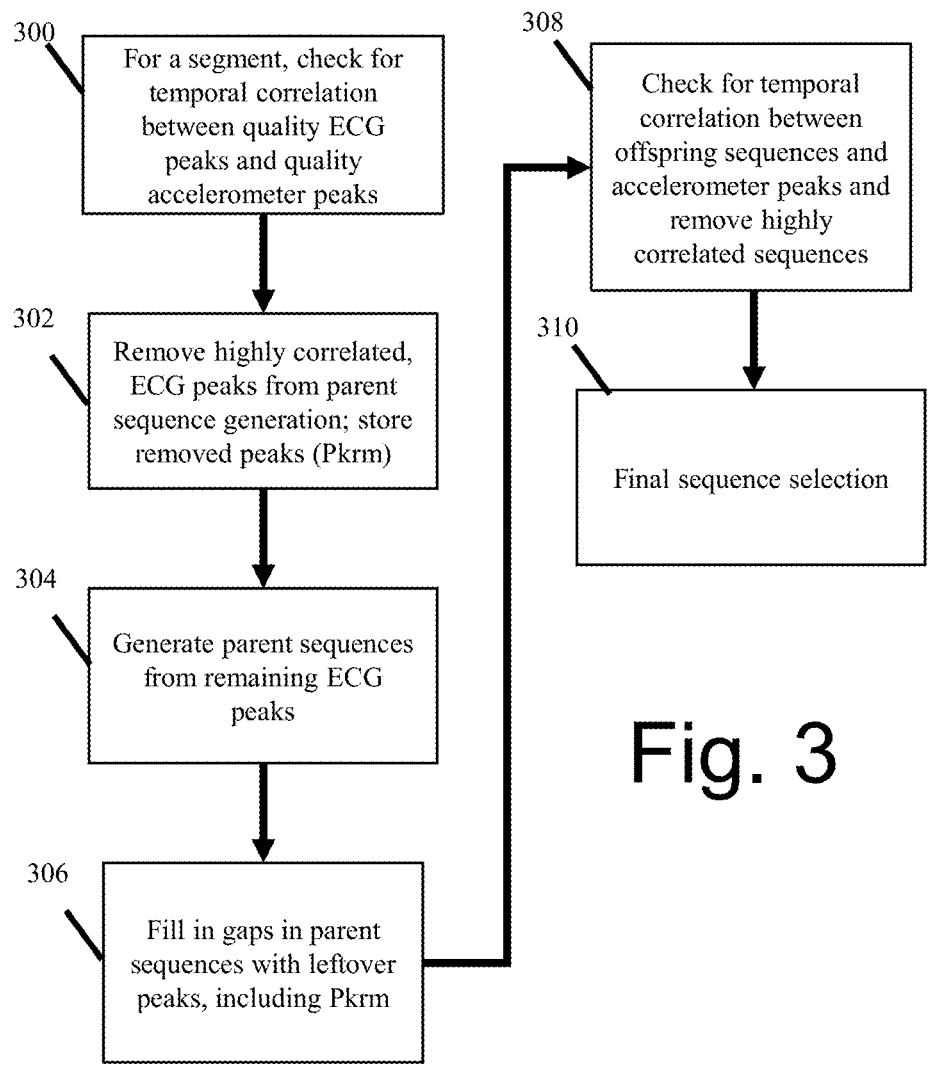
FIG. 3 is an overview flow chart of the method for locating and removing ECG peaks that are correlated to accelerometer peaks.

FIG. 3 is an overview flow chart of the method for locating and removing ECG peaks that are correlated to accelerometer peaks. In block 300, quality peaks from an ECG signal (e.g. recorded from the sensors 1a, 1b in FIG. 1) data segment are checked for temporal correlation with quality peaks from a signal, corresponding to the same segment, recorded by accelerometer 10. In block 302, ECG peaks that are temporally correlated with accelerometer 10 peaks are removed from parent sequence generation but stored as Pkrm. In particular, these correlated peaks cannot form part of parent sequences and they are considered as non-existent for the purposes of peak prominence scoring for parent sequences. In block 304, parent sequences are generated. As described in the previously mentioned publication WO/2022/086740, parent sequence generation within a data segment comprises the steps of: 1) selecting the N largest peaks (candidate peaks) that satisfy shape criteria; 2) generating possible heart beat sequences from these peaks; 3) scoring the sequences based on a variety of measures.

In block 306, gaps in parent sequences are filled in with leftover peaks, including the removed peaks Pkrm. In block 308, the resulting offspring sequences are checked for temporal correlation with the accelerometer peaks. This step, which will be further described with reference to block 516 of FIG. 5, is performed because the peak removal performed in block 302 may have been incomplete and the possible addition of Pkrm in block 302 may result in highly correlated sequences. In block 310, the remaining sequences are scored and selected.

Figure 4:
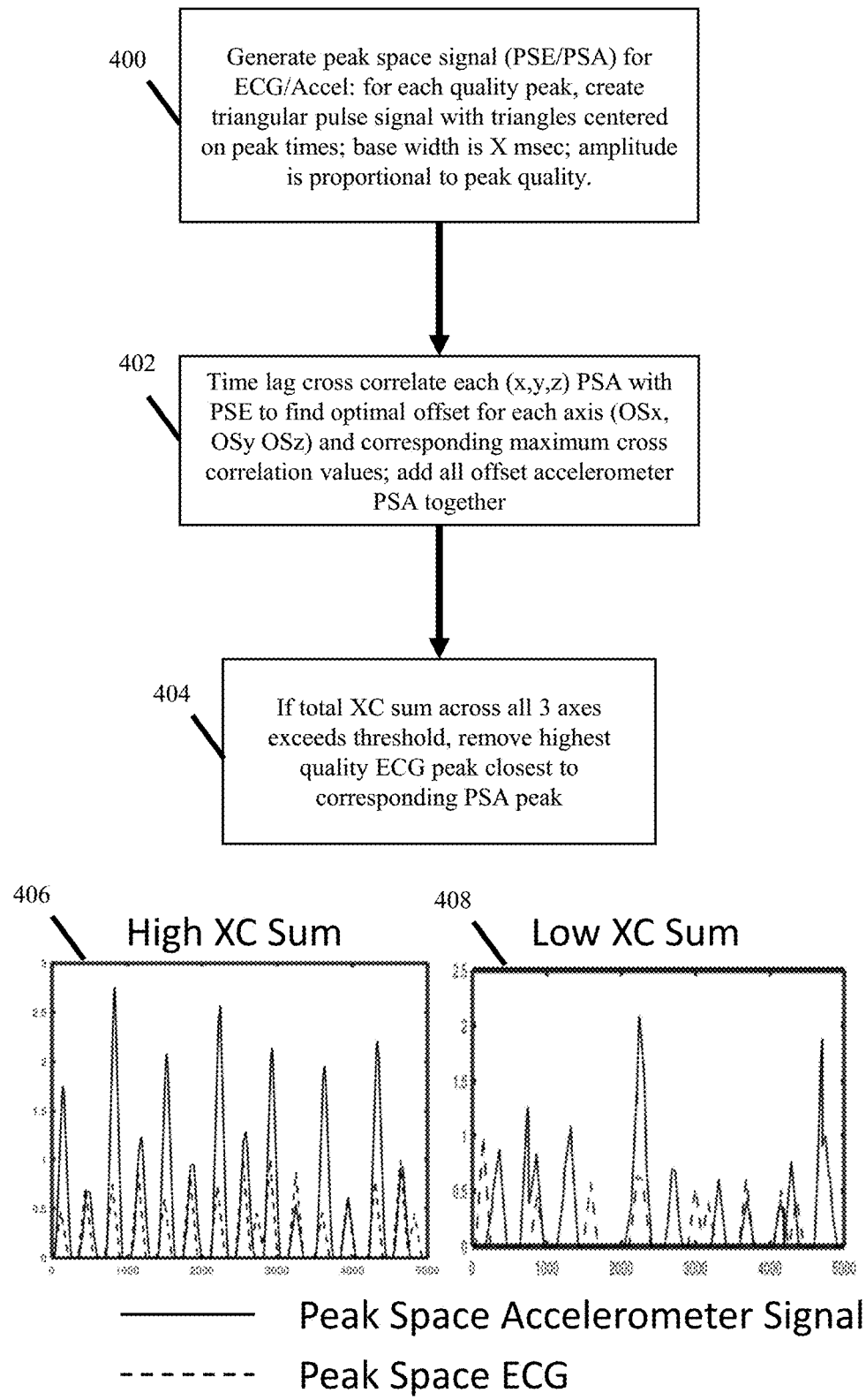
FIG. 4 is a flow chart of the preferred method for correlating ECG peaks with accelerometer peaks.

FIG. 4 is a flowchart of the preferred method for correlating ECG peaks with accelerometer peaks. In block 400, peak space signals, PSA and PSE, are generated for both ECG and accelerometer peaks respectively. A peak space signal represents peaks according to their occurrence times. Examples of peak space signals are shown in plots 406 and 408. Peaks are represented by triangles centered at the peak times with bases wide enough to capture peak time correlation features of interest. For the purposes of correlating ECG and accelerometer peak times, in the preferred embodiment, the base is 200 ms (actually, the equivalent number of samples thereof). The amplitude of the triangles is set according to some measure of peak quality, e.g. amplitude.

(For pure temporal cross-correlation, which is appropriate in some circumstances, the amplitude may be set to unity.) For the purposes of correlating ECG and accelerometer peak times, in the preferred embodiment, signal peaks with quality that do not exceed a threshold are not represented in the peak space signal; this removal prevents large numbers of low amplitude peaks (noise) from producing a spurious large cross correlation sum.

Alternative peak space transformations are possible. For example, instead of substituting a shape (e.g. a triangle, as above) for a peak, a signal may be directly transformed by for example summing a rectified (absolute value, squaring etc.) derivative/difference, possible temporal contraction/expansions, and then thresholding to eliminate noise peaks.

In block 402, each of the three (x,y,z axis) accelerometer peak space signals are separately time lagged cross correlated with the ECG peak space signal. The offset/lag between each axis' peak space signal (OSx, OSy, and OSz) and the ECG peak space signal is selected as the time difference in the cross correlation that produces the largest cross correlation value. The three offset PSA are added together, thereby generating an overall PSA. In block 404, if the sum of all three maximum values, i.e. the total cross correlation across all 3 accelerometer axes, exceeds a threshold, indicating a high quality match between the ECG and at least one accelerometer signal, each high quality ECG peak closest to an overall PSA peak is removed. Plot 406 is an example of a high quality match whereas the plot 408 is an example of a low quality match.

FIG. 5 is a flowchart of the preferred method for obtaining multi-channel ECG peak coherence times in the context of accelerometer peak cancellation. For convenience, an embodiment involving 2 ECG channels will be described, but the methodology is applicable to any number of ECG channels. In block 500, for ECG channels 1 and 2, the overall offset (OS1 and OS2) between the accelerometer and the ECG is generated as a weighted sum of the three offsets OSx, OSy and OSy, where the weighting is based on the corresponding cross correlation sum. The difference (OSA) between the overall offsets OS1 and OS2 is generated. OSA is the offset between ECG channels that maximizes the cross correlation of accelerometer induced peaks between channels 1 and 2.

In block 502, the channel 1 and 2 ECG peaks are time lagged cross correlated after removal of accelerometer induced peaks performed in block 404 of FIG. 4. The result is cross correlation signal XCE, an example of which is shown in plot 518. Because the block 404 removal may not completely eliminate all accelerometer induced peaks, the cross correlation XCE may show a peak related to the accelerometer induced peaks. Absent extreme noise, XCE will also have a relatively large value at the optimal QRS offset (OSQ) between channels. (The optimal QRS offset is the offset between channels that maximizes inter-channel coherence of QRS complexes.) In the case that there is some residual correlated random noise between channels, this will contribute to XCE at an offset of around 0. According to one embodiment, in the case of a reasonably regular heart rhythm, peaks in XCE that are shifted (to the left and/or right) by one or more RR intervals are examined, in which case there may be a peak around OSQ shifted by approximately an integer multiple of the RR interval, whereas correlated noise would not have such a shifted peak. This embodiment may also help to distinguish QRS correlations from random correlations. To the extent that motion induced peaks are less regular than the heartbeat, examination of the RR interval shifted peaks will help distinguish motion induced peaks and QRS peaks.

If there is a dominant peak OSm in XCE, it may correspond to OSA or OSQ or both. If OSm is near both OSA and also to the historical value of OSQ, OSQH (whose value is tracked as hereafter described), then control passes through block 504 to block 510. Sequences are generated as described in publication WO/2022/086740, entitled "Multi-channel Heartbeat Detection by Temporal Pattern Search," with the peak time offset set to OSm and temporal coherence probabilities reduced to reflect the possible contribution of accelerometer induced peaks to the OSm. The temporal coherence probabilities are adjusted according to the alignment between PSE and PSA. Returning to plot 408, and assuming for the purposes of illustration that all of the ECG peaks have large temporal coherence probabilities, some ECG peaks (at offset OSm) align with the accelerometer peaks while others do not. The temporal coherence probabilities are reduced according to the degree of alignment. The reduction may be statistically determined. A heuristic rule of setting the coherence probabilities to 0 when the ECG and accelerometer peaks are within 100 ms of one another has produced good results.

If an accelerometer signal is sampled at a low frequency, it may not have sharp peaks. In this case, a peak space signal need not be constructed. Rather, the more "sinusoidal" shape of the raw signal may be used directly, after preferably removing lower amplitude portions of the signal.

Block 510 transfers control to block 516, in which sequences are checked for temporal alignment with the accelerometer peaks as in block 308. Sequences that can be aligned with the accelerometer peaks are removed. Returning to plot 406, and interpreting the 14 largest ECG peaks (dashed line) as a sequence, the overall alignment between the ECG peaks and accelerometer peaks means that it is reasonably likely that the ECG peaks are caused by motion artifact. In contrast, in plot 408, the overall alignment is low, so that the ECG peaks can be taken as QRS complexes (even though a few of them may coincide accelerometer peaks due to the closeness of OSQ and OSA). As described in the previously mentioned publication WO/2022/086740, the ECG sequences may consist of a mixture of single channel peaks from different channels and peaks that align across channels.

Returning to block 502, if OSm is not close to OSA, block 506 transfers control to block 512, which uses OSm as the offset and no peak coherence probability adjustment is necessary. Control transfers again to block 516.

Returning to block 502, control transfers to block 508 if there is no dominant peak in XCE, i.e. no peak that is at least 30% larger than all other peaks, or OSm is not close to OSQH. Block 508 transfers control to block 514, which uses the subsidiary peak time if any of the major peaks are close to OSQH. Control again passes to block 516.

Figure 6A:
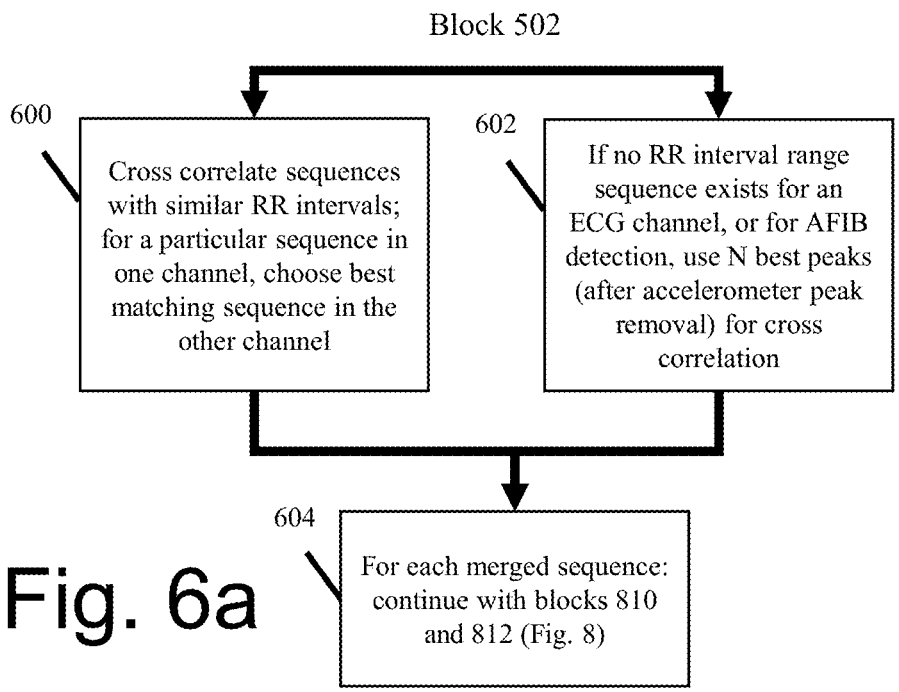
FIG. 6a is a flowchart of the ECG peak selection process for the purpose of creating an ECG peak space signal that is cross-correlated according to the flowchart of FIG. 5.

FIG. 6a is a flowchart of the ECG peak selection process for the purpose of creating the ECG peak space signal that is cross-correlated in block 502. As shown in block 600, if there are sequences in different channels with similar RR intervals, they are cross correlated, preferably by creating peak space signals. The correlation is performed with a tighter tolerance than accelerometer peak correlation; if triangles are used in a peak space signal, the base of the triangles is 30 ms-40 ms. If more than one sequence exists in a channel that corresponds to the same RR interval range in another channel, the pertinent sequences in the first channel are cross correlated with the second channel sequence and the one that best matches is selected as the partner for the second channel sequence. If no sequence exists in a second channel that is within a first channel sequence's RR interval range, then the N best peaks in the second channel are used, as shown in block 602. In the case of atrial fibrillation (or other irregular rhythm) detection, the N best peaks from both signals are cross correlated. In an alternative embodiment, different possible atrial fibrillation sequences are generated in each channel and cross correlated.

After a first cross correlation, it is possible to remove peaks and perform another cross-correlation to refine the match. In block 604, each merged sequence from blocks 600 or 602 are treated as parent sequences and processed according to the multi-channel procedure described in the multi-channel patent application and as described with reference to blocks 810 and 812 of FIG. 8 herein. (For the purpose of description, a sequence from one channel is considered merged even if there are no matching peaks from the other channel from blocks 600 or 602.)

Figure 6B:
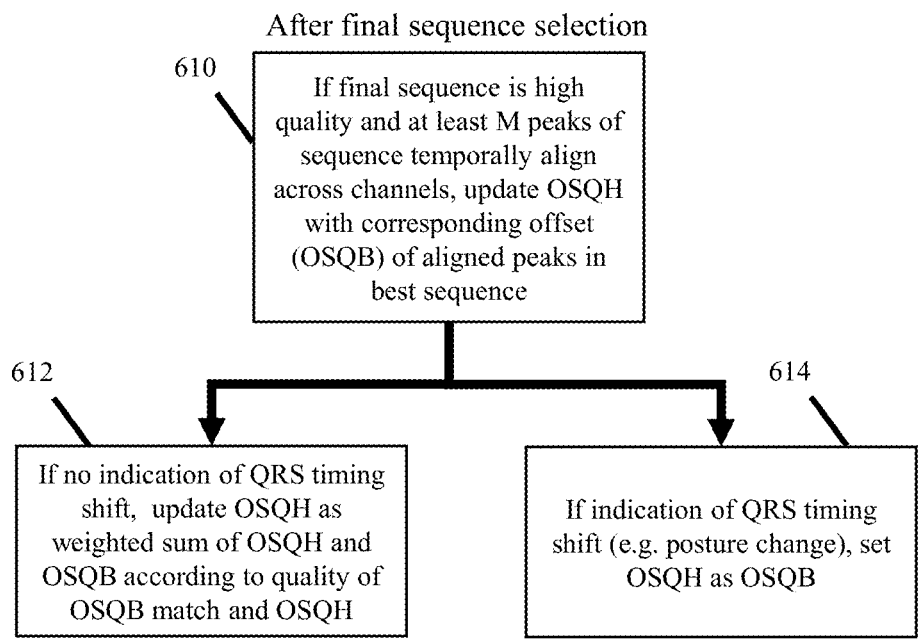
FIG. 6b is a flowchart of the process for updating a historical QRS offset that is referenced in FIG. 5.

Even though a high quality sequence may be the desired final heart beat sequence, the ECG cross-correlation is nonetheless performed to update the channel time offset OSQH as shown in block 610 of FIG. 6b. As shown in block 614, for a particular channel, if no high quality sequence exists, the N best (highest probability) peaks are used to create the peak space signal. For a 5 s or 7.5 s segment, an exemplary value of N is 20. If the cross correlation shows clean harmonics at the average RR interval, then the RR interval may be selected without additional searching and the corresponding channels' sequences merged to create a final sequence.

FIG. 6b is a flowchart of the process for updating the historical QRS offset QRSH. In block 610, if the final sequence is high quality and at least M peaks of sequence temporally align across channels, OSQH is updated with corresponding offset (OSQB) of aligned peaks in best sequence. If either of these conditions is not met, then OSQH is not updated. The optimal case is that the true QRS offset remains stable over time. However, in some cases, the true QRS offset may change gradually if, for example, the location of a recording sensor changes gradually. In other cases, the true QRS offset may change abruptly and frequently. It may be possible to associate some of these abrupt changes with external information, which can be used to update the likelihood of a particular offset. For example, a posture change may be reflected in the accelerometer signal and a heart rhythm change may be detectable by analyzing QRS morphology/rhythm. Sensor location changes may be detectable in a variety of ways, e.g. through an optical sensor that registers to natural or man-made (e.g. marker) landmark.

If any such indication of a QRS timing shift exists, then in block 614, OSQH is set to OSQB. Otherwise, in block 612, OSQH is updated as a weighted sum of OSQH and OSQB according to the quality of both estimates. Note that this updating also occurs in the case where an abrupt QRS timing shift has occurred but there is no exogenous indication of such a shift. In this case, if OSQB is high quality and differs greatly from OSQH, then OSQH will be set at or near OSQB (regardless of the quality estimate of the prior OSQH).

Figure 7:
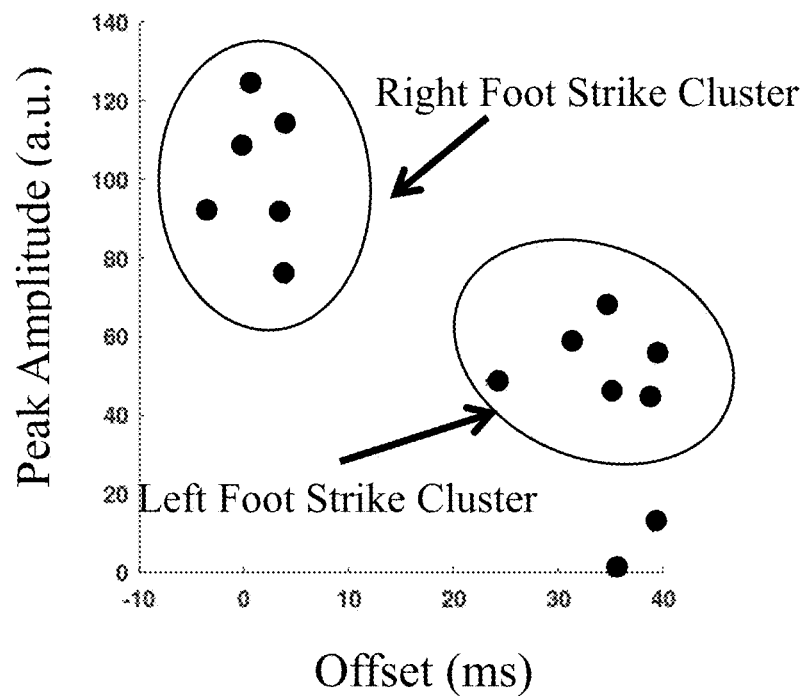
FIG. 7 is a plot of a single axis offset between accelerometer and ECG peaks that shows two groups of offsets that cluster by time and amplitude.

FIG. 7 is a plot of a single axis offset (e.g. OSx) between accelerometer and ECG peaks that shows two groups of offsets that cluster by time and amplitude. The plot corresponds to a recording from an ambulatory human's waist. It is likely that the different delays and amplitudes correspond to left and right foot strikes respectively. In such a case, instead of a single offset, different offsets may be derived by clustering according to time and/or amplitude. In terms of the peak space representation, instead of locating a single offset that maximizes the cross correlation, two different offsets may be located whose average sum is greater than the maximum single offset sum. In addition or alternatively, the clustering quality (i.e. relative areas of the ellipses that enclose the clusters in FIG. 7) may be used as evidence of the quality of the match.

Figure 8:
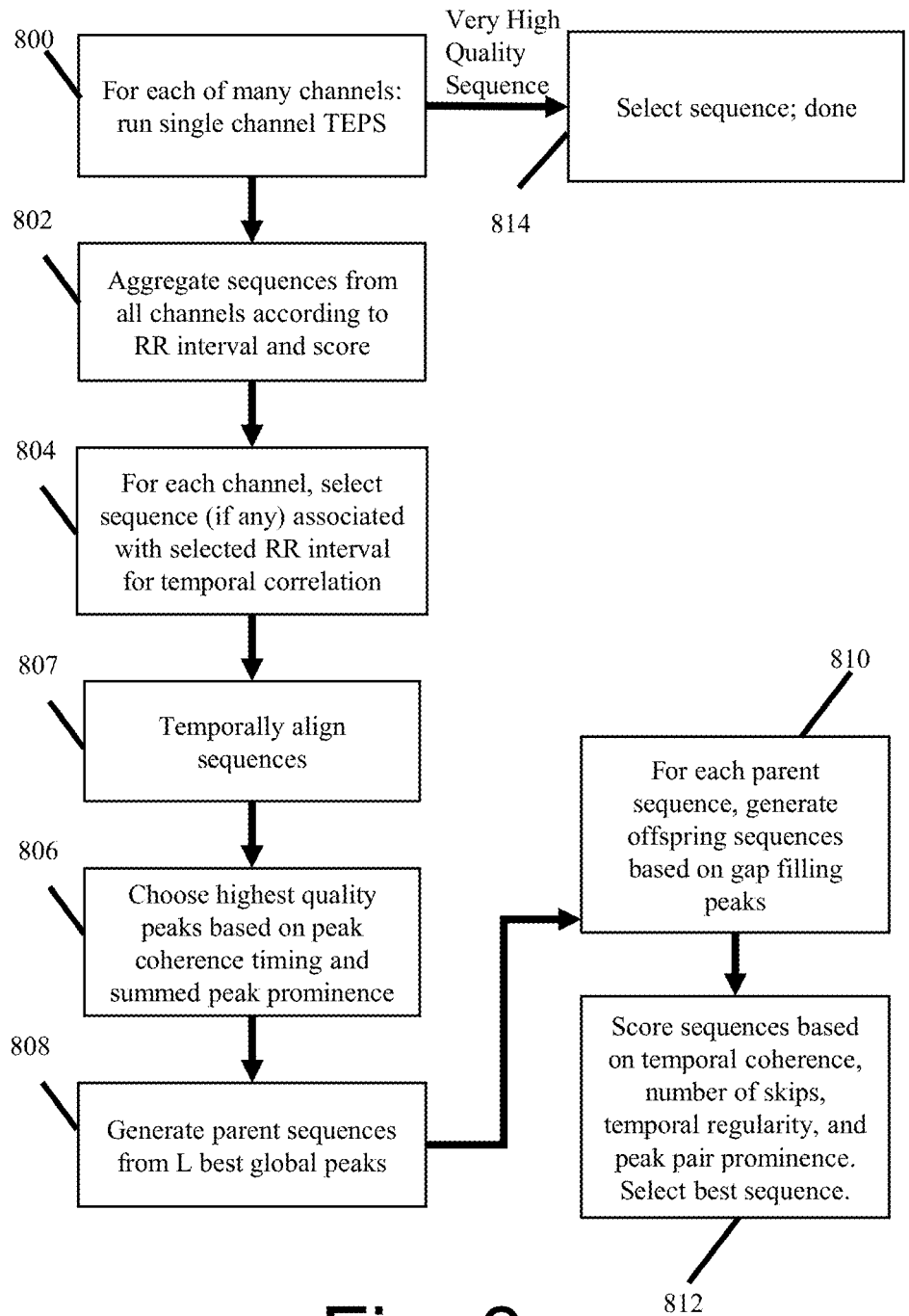
FIG. 8 is a flowchart of QRS detection method that is applicable to a potentially large number of channels.

FIG. 8 is a flowchart of QRS detection method that is applicable to a potentially large number of channels. For example, in the case of the NInFEA database, which includes records of abdominal ECGs recorded from pregnant women, there are dozens of "unipolar" leads, which correspond to hundreds of bipolar leads (channels). Depending on the fetal orientation (if known), it may be possible to select a subset of these channels as likely to yield the highest quality fetal ECGs. Also, if the current segment is not the first one in a record, the best leads associated with the prior segment may be prioritized in the search. In any event, there may be many channels that need to be searched and correlated to obtain an optimal fetal heartbeat sequence.

In block 800, the temporal pattern search procedure (TEPS) described above and in publication WO/2022/086740, entitled "Multichannel Heartbeat Detection by Temporal Pattern Search," is run for a potentially large number of channels. (TEPS has been run on the envelopes extracted from ultrasound recordings in the NInFEA database to derive heartbeat time series that match, to a high degree, the heartbeat time series obtained from the fetal ECGs. In this case, the second difference "temporal distance" is decreased to reflect the shorter fetal heartbeat.) The combinatoric sequence search and selection described in U.S. Pat. No. 9,402,557 and/or the above mentioned patent publication may be carried out to obtain an optimal sequence for each channel. Alternatively, instead of performing a combinatoric sequence search to find the optimal sequence for each channel, autocorrelation in peak space may be performed to find a most likely RR interval and corresponding quality as indicated by the correlation sum. The sequence corresponding to the most likely RR interval may be extracted but this is not necessary until block 804 (according to which sequences need not be obtained for low quality RR intervals). If for any channel a very high quality sequence is obtained, control transfers to block 814, which selects the high quality sequence and terminates.

Figure 9:
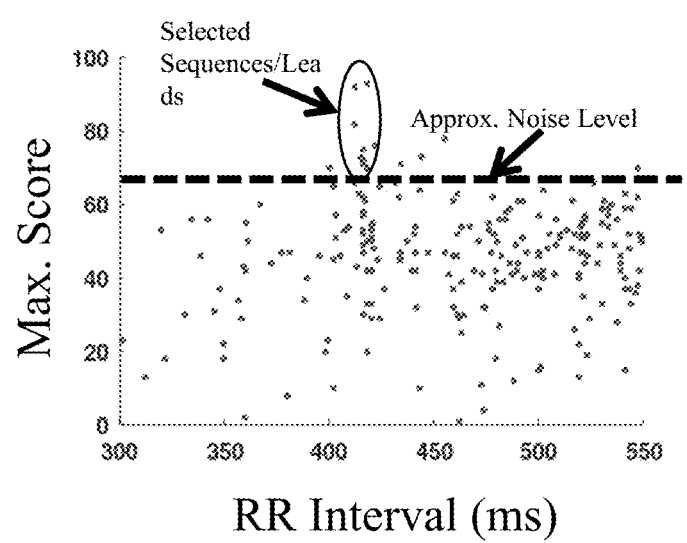
FIG. 9 is a plot of RR interval vs. sequence score that is pertinent to the channel/sequence selection methods described with reference to FIG. 8.

Otherwise, in block 802, the RR intervals and scores are aggregated. FIG. 9 is a plot of an RR interval/score aggregation which shows a cluster of highest quality RR intervals around 420 ms. More generally, a score weighted RR interval histogram is generated, and if it has a dominant peak whose amplitude exceeds a threshold, the RR interval associated with the peak is chosen. The histogram is preferably binned over RR interval ranges, e.g. 20 ms, so a single RR interval may be taken as the score weighted average of RR intervals within the maximum RR interval range. Other clustering methods are possible to determine whether an RR interval range is statistically different from noise.

In block 804, the sequences/channels associated with the cluster are selected. In block 807, the sequences are temporally aligned, preferably by peak space cross correlation. Multiple channels are simultaneously cross correlated. The channel with the maximum sum of cross correlation values is first chosen and added to the signal with which it is most correlated to create a merged signal. This merged signal is then cross-correlated with the remaining signals. The above process is repeated until all channels have been merged. In block 806, the highest quality peaks are chosen based on peak timing coherence (i.e. the sum of all the above mentioned cross correlation) and peak prominence. Blocks 808, 810 and 812 then follow the procedure described in the above mentioned Multichannel Heartbeat Detection publication.

In block 808, parent sequences are generated from the L best global peaks (i.e. peaks merged across channels). In block 810, offspring sequences are generated by filling gaps in parent sequences, and in block 812, the offspring sequences are scored based on temporal coherence, peak prominence and number of skips. The highest scoring sequence is selected.

According to exemplary data, at a 256 Hz sampling rate with no inherent time difference between true beats, the time difference probability for true beats falls off sharply from a 0 sample difference to a 2 sample difference, with very low probabilities for time differences greater than 2 samples.

Figure 10:
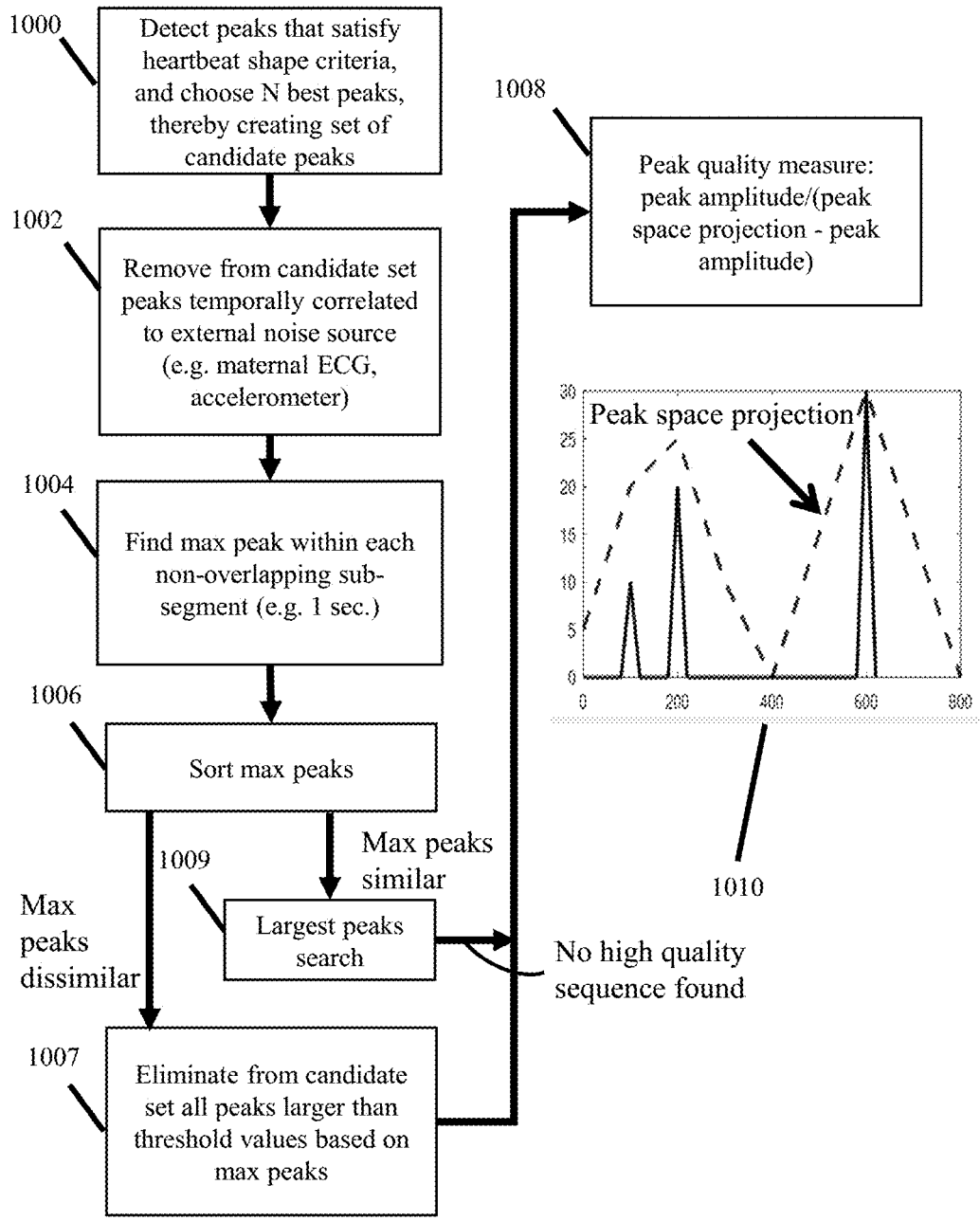
FIG. 10 is a flowchart of the selective peak removal methods of the present invention, including peak removal associated with an estimate of the QRS complex dynamic range.

FIG. 10 is a flowchart of the selective peak removal methods associated with block 103 of FIG. 2. In block 1000, a set of peaks is detected that satisfy the shape criteria for heartbeats. In block 1002, peaks that are temporally correlated to external noise source are removed according to the methods hereinabove described. Depending on the application, the noise source may be maternal QRS complexes, motion artifacts that are reflected in an accelerometer signal or other external signal. In block 1004, the maximum peak (in second difference space) within each non-overlapping (e.g. 1 sec.) sub-segment is found. In block 1006, these maximum peaks are sorted. If the maximum peaks are similar in shape/size, then the largest peaks across the entire segment are searched and scored in block 1009, which represents above described peak searching and scoring techniques. To handle the possibility of large amplitude artifacts that mimic heart beat shapes, the scoring preferably includes peak shape similarity criteria. If no high quality sequence is found, the largest peaks may be eliminated and control passed to block 1008. If the maximum peaks are dissimilar, indicating large shifts in signal dynamic range, control transfers to block 1007, where all peaks above a value that depends on the amplitudes of the maximum peaks are eliminated. The value is preferably a multiple of the median of the maximum peaks, but also may be a more complicated function such as a weighted sum of the maximum peaks.

After the above mentioned elimination in block 1007, in block 1008, remaining peaks are given a peak quality measure that depends on the relative amplitude of a peak compared to its surrounding peaks. In turn, the surrounding peak amplitude function is preferably a peak space projection function: the triangles (or other shape) of the peak space function are expanded such that their bases extend over e.g. 200 ms on either side of the peak, and the triangle values at any time are summed. An example of a peak space projection function is shown in plot 1010; between the first and second peaks (100 ms-200 ms), the triangles from the two peaks are added together.

Although the above mentioned methods are described with reference to sinus rhythm detection, the methods herein are applicable to any type of heart rhythm.

Correlation based heartbeat likelihood measures may be obtained by comparing statistics gathered from processing signals where there is a corresponding gold standard heartbeat reference. For example, for multiple-channel ECG peak time coherence correlation, the correlation measures for sequences may be compared against the sequence quality, which is based on a match with the gold standard.

The present invention encompasses many other types of correlation techniques. For example, to correlate heart beat sequences associated with different channels, sequences may be grouped according to RR interval (e.g. FIG. 9), relatively high temporal regularity and similar overall "phase," which may be determined by some function of modulo(peak time/RR interval). Furthermore, the correlation may be carried out by a neural network that is trained on multichannel peak times or peak space shapes described herein as input with output desired correlation measures or even final measures of joint sequence quality (in which case the correlation is implicitly performed by the neural network.)

The invention claimed is:

1. A method for detecting a cardiac rhythm comprising the steps of:
   a. receiving a first signal from a first sensor, wherein the first signal is a cardiac signal;
   b. receiving a second signal from a second sensor;
   c. detecting and selecting peaks in each of the first and second signals, thereby generating first and second sets of peaks, wherein the first set of peaks corresponds to at least two mutually exclusive heart beat sequences;
   d. temporally correlating a subset of the first set of peaks with the second set of peaks over variable time offsets, thereby deriving corresponding sets of correlation measures that apply to particular time offsets between the sets of peaks;
   e. determining a heartbeat likelihood measure for at least one of the peaks in the first or second sets based on at least one of the sets of correlation measures;
   f. detecting a cardiac rhythm based on the heartbeat likelihood measure.

2. The method of claim 1 wherein the second signal is related to a noise source such that the correlation measures are negatively related to heartbeat likelihood.

3. The method of claim 2 wherein the noise source is motion and the second signal is an accelerometer signal.

4. The method of claim 1 wherein the first and second signals are electrocardiograms such that the correlation measures are positively related to heartbeat likelihood.

5. The method of claim 4 wherein the subset of the first set of peaks represents a possible heartbeat sequence.

6. The method of claim 5 wherein the second signal is a cardiac signal and the second set of peaks represents a possible heartbeat sequence, and further comprising the step of merging the first and second sets of peaks to generate a merged sequence.

7. The method of claim 1 wherein the temporal correlation is further based on a measure of peak quality.

8. The method of claim 1 wherein the correlation measures are determined by performing a signal cross correlation.

9. The method of claim 8 wherein the cross correlation is carried out by assigning to each peak a shape characterized by a maximum value at each corresponding peak time.

10. The method of claim 1 further comprising the step of selecting the subset of the first set of peaks according to peak quality criteria.

11. The method of claim 1 further comprising the step of selecting the second set of peaks according to peak quality criteria.

12. The method of claim 1 wherein the cardiac rhythm is detected by selecting a sequence of peaks that include at least one peak from the subset of the first set of peaks.

13. The method of claim 1 wherein the heartbeat likelihood measure applies to an individual peak within the subset of the first set of peaks.

14. The method of claim 1 further comprising the step of performing a heartbeat sequence search that excludes peaks within a subset of the subset of the first set of peaks that are highly correlated to the second set of peaks.

15. The method of claim 1 wherein the first signal is an electrocardiogram.

16. The method of claim 1 wherein the subset of the first set of peaks does not correspond to a possible heartbeat sequence, and further comprising the step of generating possible heartbeat sequences from the subset of the first set of peaks.

17. The method of claim 1 wherein the step of detecting a cardiac condition comprises the step of selecting a sequence of possible heartbeats based on the heartbeat likelihood measure.

18. The method of claim 17 wherein the heartbeat likelihood measure is further based on sequence characteristics.

19. The method of claim 18 wherein the sequence characteristics include temporal regularity and skips.

20. The method of claim 1 wherein each of the sets of correlation measures contains a single correlation measure that applies to a sequence of peaks.

21. The method of claim 1 wherein each of the sets of correlation measures includes a plurality of correlation measures that apply to corresponding peaks.

22. A method for detecting a cardiac rhythm comprising the steps of:
  a. receiving a first signal from a first sensor, wherein the first signal is a cardiac signal;
  b. detecting and selecting a first set of peaks within the first signal that correspond to at least two mutually exclusive heartbeat sequences;
  c. temporally correlating a subset of the first set of peaks with the first signal or a second signal over variable time offsets, thereby deriving correlation measures that correspond to time offsets, wherein at least one of the correlation measures is at least partly a decreasing function of time from a peak within the subset;
  d. determining a cardiac rhythm based on at least one of the correlation measures.

23. The method of claim 22 wherein the correlation measures are implicitly determined by a neural network.

24. The method of claim 22 wherein the decreasing function is linear.

25. The method of claim 22 wherein the shape of the decreasing function corresponds to a shape with a width that is selected according to an expected precision of temporal correlation, so that wider shapes are associated with lower precision.

26. The method of claim 22 wherein the decreasing function results from transformations of the first signal.

27. The method of claim 22 wherein the decreasing function results from centering a preselected shape on each of the peaks within the subset of the first set of peaks.

28. The method of claim 27 wherein the subset of the first set of peaks is selected according to individual peak quality.

29. The method of claim 22 wherein the second signal is associated with a noise source such that the subset has a probability of being noise as an increasing function of the correlation measures.

30. The method of claim 22 wherein the first and second signals are electrocardiograms.

31. The method of claim 30 wherein the subset has a probability of being heart beats as an increasing function of the correlation measures.

32. The method of claim 22 wherein the correlation measures are obtained from signal cross correlation.

33. The method of claim 22 wherein the correlation measures are obtained from clustering.

34. The method of claim 22 wherein the subset of the first set of peaks is a proper subset.

35. The method of claim 34 wherein the subset of the first set of peaks is a possible heartbeat sequence.

36. The method of claim 22 further comprising the step of detecting a second set of peaks in the second signal, and wherein the correlation measures depend on the temporal alignment of the first set of peaks with the second set of peaks.

37. The method of claim 22 further comprising the step of determining an optimal time offset between the first set of peaks and corresponding peaks within the second signal, and the cardiac rhythm is selected according to a correlation measure that corresponds to the optimal time offset.

38. The method of claim 22 further comprising the step of estimating an average RR interval associated with a time offset between the first set of peaks and peaks shifted by time periods on the order of one or more RR intervals, wherein the shifted peaks are either (i) other members within the first set of peaks, or (ii) peaks within the second signal.

39. A method for detecting a cardiac rhythm comprising the steps of:
  a. receiving a first signal from a first sensor, wherein the first signal is a cardiac signal;
  b. detecting and selecting a set of peaks within the first signal that correspond to at least two mutually exclusive heartbeat sequences;
  c. determining a heartbeat likelihood value for each of the set of peaks;
  d. selecting a proper subset of the first set of peaks based on the heartbeat likelihood values;
  e. temporally correlating the subset of the first set of peaks with the first signal or another signal over variable time offsets, thereby deriving correlation measures that correspond to time offsets,
  f. detecting a cardiac rhythm based on at least one of the correlation measures.

40. The method of claim 39 wherein the subset forms a first possible heartbeat sequence.

41. The method of claim 40 further comprising the step of selecting a second subset of the first set of peaks that corresponds to a sequence that is mutually exclusive to the first possible heartbeat sequence, and performing step e with the second subset.

42. The method of claim 39 wherein the subset consists of the peaks with the highest likelihood values, such that the subset does not necessarily correspond to a physiologically permissible heartbeat sequence.

43. The method of claim 39 wherein the first and second signals are electrocardiograms.

44. A method for detecting a cardiac rhythm comprising the steps of:
  a. receiving a first signal from a first sensor, wherein the first signal is a cardiac signal;
  b. receiving a second signal from a second sensor, wherein the second signal is correlated with a noise source;
  c. detecting peaks in each of the first and second signals, thereby generating first and second sets of peaks;

d. temporally correlating the first set of peaks with the second set of peaks over variable time offsets, thereby deriving corresponding sets of correlation measures that apply to particular time offsets between the sets of peaks;
e. determining a heartbeat likelihood measure for one of the peaks within the first set according to at least one of the correlation measures;
f. detecting a cardiac rhythm based on the heartbeat likelihood measure.

* * * * *